United States Patent
Gosset et al.

(10) Patent No.: US 12,358,977 B2
(45) Date of Patent: Jul. 15, 2025

(54) TREATMENT OF ACUTE EXACERBATIONS OF CHRONIC OBSTRUCTIVE PULMONARY DISEASE BY ANTAGONISM OF THE IL-20R

(71) Applicants: INSERM (INSTITUT NATIONAL DE LA SANTE ET DE LA RECHERCHE MEDICALE), Paris (FR); INSTITUT PASTEUR DE LILLE, Lille (FR); UNIVERSITE DE LILLE 1 SCIENCES ET TECHNOLOGIES, Villeneuve d'Ascq (FR); CENTRE NATIONAL DE LA RECHERCHE SCIENTIFIQUE (CNRS), Paris (FR); UNIVERSITE DE DROIT ET DE LA SANTE DE LILLE 2, Lille (FR)

(72) Inventors: Philippe Gosset, Lille (FR); Muriel Pichavant, Lille (FR); Magdiel Perez-Cruz, Lille (FR); Bachirou Kone, Lille (FR)

(73) Assignees: INSERM (INSTITUT NATIONAL DE LA SANTE ET DE LA RECHERCHE MEDICALE), Paris (FR); INSTITUT PASTEUR DE LILLE, Lille (FR); UNIVERSITE DE LILLE 1 SCIENCES ET TECHNOLOGIES, Villeneuce d'Ascq (FR); CENTRE NATIONAL DE LA RECHERCHE SCIENTIFIQUE (CNRS), Paris (FR); UNIVERSITE DE DROIT ET DE LA SANTE DE LILLE 2, Lille (FR)

( * ) Notice: Subject to any disclaimer, the term of this patent is extended or adjusted under 35 U.S.C. 154(b) by 387 days.

(21) Appl. No.: 16/507,126

(22) Filed: Jul. 10, 2019

(65) Prior Publication Data
US 2019/0330330 A1 Oct. 31, 2019

Related U.S. Application Data

(63) Continuation of application No. 15/525,799, filed as application No. PCT/EP2015/077365 on Nov. 23, 2015, now abandoned.

(30) Foreign Application Priority Data

Nov. 24, 2014 (EP) .................................... 14306868

(51) Int. Cl.
*A61K 39/395* (2006.01)
*C07K 16/24* (2006.01)
*C07K 16/28* (2006.01)
*A61K 39/00* (2006.01)

(52) U.S. Cl.
CPC ........ *C07K 16/244* (2013.01); *C07K 16/2866* (2013.01); *C07K 16/2887* (2013.01); *A61K 39/00* (2013.01); *A61K 2039/505* (2013.01); *C07K 2317/76* (2013.01)

(58) Field of Classification Search
CPC .......... C07K 16/2866; A61K 2039/505; A61P 11/00
See application file for complete search history.

(56) References Cited

U.S. PATENT DOCUMENTS

2005/0142108 A1* 6/2005 Grunig ................ C07K 16/244
424/85.2

OTHER PUBLICATIONS

Goel et al. Plasticity within the Antigen-Combining Site May Manifest as Molecular Mimicry in the Humoral Immune Response. J. Immunol. 2004; 173:7358-7367.*
Sapey et al. COPD exacerbations ? 2: Aetiology. Thorax. Mar. 2006; 61(3): 250-258.*
Myles et al. Signaling via the IL-20 receptor inhibits cutaneous production of IL-1β and IL-17A to promote infection with methicillin-resistant *Staphylococcus aureus*. Nat Immunol. Aug. 2013;14(8):804-11.*
Evensen, A.E. Management of COPD Exacerbations. Am Fam Physician. Mar. 1, 2010;81(5):607-13.*
Liu et al. Emerging Biological Functions of IL-17A: A New Target in Chronic Obstructive Pulmonary Disease? Front Pharmacol. Jul. 2, 2021:12:695957.*
Ding et al. IL-17 Aggravates Pseudomonas aeruginosa Airway Infection in Acute Exacerbations of Chronic Obstructive Pulmonary Disease. Front Immunol. Jan. 13, 2022:12:811803.*
Chen et al. Alterations of plasma inflammatory biomarkers in the healthy and chronic obstructive pulmonary disease patients with or without acute exacerbation. J Proteomics. Jun. 6, 2012;75(10): 2835-43.*

* cited by examiner

*Primary Examiner* — Dong Jiang
(74) *Attorney, Agent, or Firm* — WCF IP

(57) ABSTRACT

The present invention relates to methods and pharmaceutical compositions for the treatment of acute exacerbation of chronic obstructive pulmonary disease. In particular, the present invention relates to a method of treating acme exacerbation of chronic obstructive pulmonary disease in a subject in need thereof comprising administering the subject with a therapeutically effective amount of an antagonist of IL-20 cytokines.

6 Claims, 8 Drawing Sheets

Figure 1:
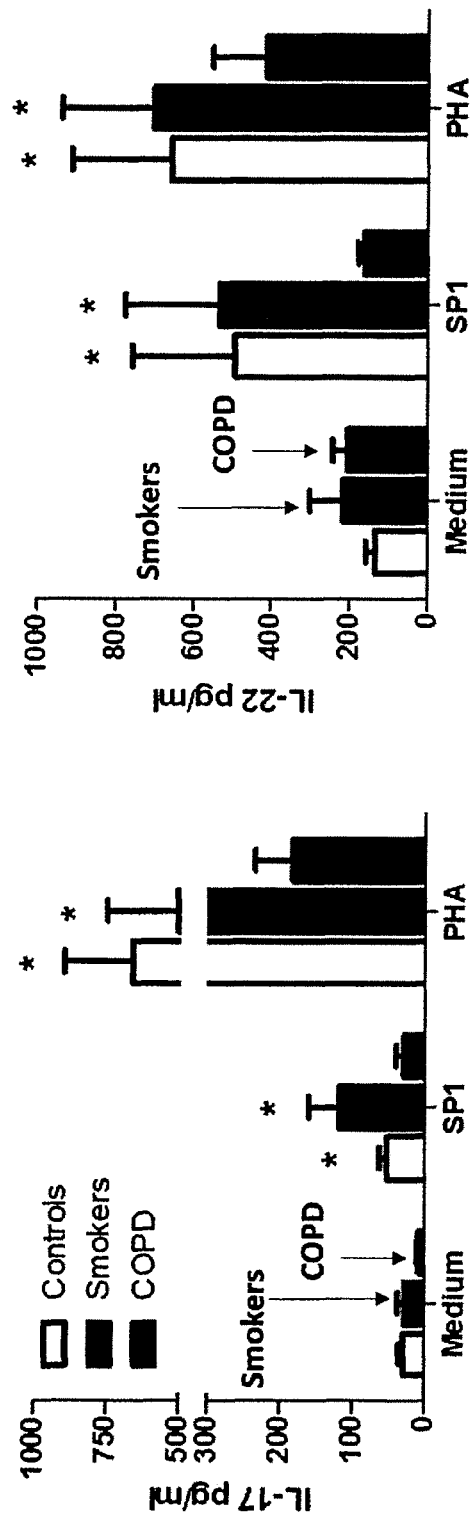

TREATMENT OF ACUTE EXACERBATIONS OF CHRONIC OBSTRUCTIVE PULMONARY DISEASE BY ANTAGONISM OF THE IL-20R

The present invention relates to methods and pharmaceutical compositions for the treatment of acute exacerbation of chronic obstructive pulmonary disease.

BACKGROUND OF THE INVENTION

Chronic obstructive pulmonary disease (COPD) represents a severe and increasing global health problem. By 2020, COPD will have increased from 6th (as it is currently) to the 3rd most common cause of death worldwide. In the United States, COPD is believed to account for up to 120,000 deaths per year. The clinical course of COPD is characterized by chronic disability, with intermittent, acute exacerbations which may be triggered by a variety of stimuli including exposure to pathogens, inhaled irritants (e.g., cigarette smoke), allergens, or pollutants. "Acute exacerbation" refers to worsening of a subject's COPD symptoms from his or her usual state that is beyond normal day-to-day variations, and is acute in onset. Acute exacerbations of COPD greatly affect the health and quality of life of subjects with COPD. Acute exacerbation of COPD is a key driver of the associated substantial socioeconomic costs of the disease. Multiple studies have also shown that prior exacerbation is an independent risk factor for future hospitalization for COPD. In conclusion, exacerbations of COPD are of major importance in terms of their prolonged detrimental effect on subjects, the acceleration in disease progression and the high healthcare costs. However up to now, there is no method for the treatment of acute exacerbation of COPD.

Based on their genes and protein structures, IL-19, IL-20 and IL-24 form a subgroup in the IL-10 cytokine family: the IL-20 cytokines that are very close to IL-22. IL-19 and IL-20 act via a receptor complex that consists of the IL-20R1 and IL-20R2 chains present on epithelial and antigen-presenting cells. IL-20 and IL-24 are additionally able to signal via a second receptor complex (IL-22R1/IL-20R2). Recent reports have shown that IL-20 cytokines function as proinflammatory cytokines that are involved in inflammatory diseases, such as psoriasis, rheumatoid arthritis, atherosclerosis, ischemic stroke, and renal failure. This cytokine family affects the growth and differentiation of epithelial cells but also induce a number of chemokines, anti-microbial peptides and growth factors. Given their origins and their properties, these cytokines probably control the cross-talk between immune and resident cells during mucosal immunity and wound healing. However the role of IL-20 cytokines has never been investigated in acute exacerbation of COPD.

SUMMARY OF THE INVENTION

The present invention relates to methods and pharmaceutical compositions for the treatment of acute exacerbation of chronic obstructive pulmonary disease. In particular, the present invention is defined by the claims.

DETAILED DESCRIPTION OF THE INVENTION

Bacterial infections are a major cause of disease exacerbation in lung inflammatory disorders including chronic obstructive pulmonary disease (COPD). In this disease, bacterial susceptibility is related to a defect in Th17 cytokines whereas IL-20 cytokines are overexpressed in the lung. In parallel, an immunosuppressive role for IL-20 cytokines has been identified during infection that can be therapeutically targeted to alter susceptibility to infection.

Accordingly, the present invention relates to a method of treating acute exacerbation of chronic obstructive pulmonary disease in a subject in need thereof comprising administering the subject with a therapeutically effective amount of an antagonist of IL-20 cytokines.

As used herein the term "acute exacerbation" has its general meaning in the art and refers to worsening of a subject's COPD symptoms from his or her usual state that is beyond normal day-to-day variations, and is acute in onset. Typically, the acute exacerbation of COPD is manifested by one or more symptoms selected from worsening dyspnea, increased sputum production, increased sputum purulence, change in color of sputum, increased coughing, upper airway symptoms including colds and sore throats, increased wheezing, chest tightness, reduced exercise tolerance, fatigue, fluid retention, and acute confusion, and said method comprises reducing the frequency, severity or duration of one or more of said symptoms. Acute exacerbation may have various etiologies, but typically may be caused by viral infections, bacterial infections, or air pollution. For example, approximately 50% of acute exacerbations are due primarily to the bacteria *Streptococcus pneumoniae*, *Haemophilus influenzae*, and *Moraxella catarrhalis* (all of them causing pneumonia). Viral pathogens associated with acute exacerbations in subjects with COPD include rhinoviruses, influenza, parainfluenza, coronavirus, adenovirus, and respiratory syncytial virus.

In some embodiments, the acute exacerbation of COPD is caused by a bacterial infection. In some embodiments, the acute exacerbation of COPD is caused by a viral infection. In some embodiments, the acute exacerbation of COPD is caused by air pollution.

In some embodiments, the subject experienced an acute exacerbation of COPD or is at risk of experiencing an acute exacerbation of COPD. In some embodiments, the subject has experienced at least one acute exacerbation of COPD in the past 24 months. In one particular embodiment, the subject has experienced at least one acute exacerbation of COPD in the past 12 months. In some embodiments, subject is a frequent exacerbator. As used herein the term "frequent exacerbator" refers to a subject who suffers from or is undergoing treatment for COPD and who experiences at least 2, and more typically 3 or more, acute exacerbations during a 12 month period.

In some embodiments, "treating" refers to treating an acute exacerbation of COPD, reducing the frequency, duration or severity of an acute exacerbation of COPD, treating one or more symptoms of acute exacerbation of COPD, reducing the frequency, duration or severity of one or more symptoms of an acute exacerbation of COPD, preventing the incidence of acute exacerbation of COPD, or preventing the incidence of one or more symptoms of acute exacerbation of COPD, in a human. The reduction in frequency, duration or severity is relative to the frequency, duration or severity of an acute exacerbation or symptom in the same human not undergoing treatment according to the methods of the present invention. A reduction in frequency, duration or severity of acute exacerbation or one or more symptoms of acute exacerbation may be measured by clinical observation by an ordinarily skilled clinician with experience of treating COPD subjects or by subjective self evaluations by the subject undergoing treatment. Clinical observations by an ordinarily skilled clinician may include objective measures of lung function, as well as the frequency with which intervention is required to maintain the subject in his or her most stable condition, and the frequency of hospital admission and length of hospital stay required to maintain the subject in his or her most stable condition. Typically, subjective self evaluations by a subject are collected using industry-recognized and/or FDA-recognized subject reported outcome (PRO) tools. Such tools may allow the subject to evaluate specific symptoms or other subjective measures of quality of life. An example of one subject reported outcome tool is Exacerbations from Pulmonary Disease Tool (EXACT-PRO), which is currently being developed for evaluating clinical response in acute bacterial exacerbations by United BioSource Corporation along with a consortium of pharmaceutical industry sponsors in consultation with the FDA.

In some embodiments, the treatment is a prophylactic treatment. As used herein, the term "prophylactic treatment" refer to any medical or public health procedure whose purpose is to prevent a disease. As used herein, the terms "prevent", "prevention" and "preventing" refer to the reduction in the risk of acquiring or developing a given condition, or the reduction or inhibition of the recurrence or said condition in a subject who is not ill, but who has been or may be near a subject with the disease.

As used herein, the term "IL-20 cytokines" has its general meaning in the art and refers to a subgroup in the IL-10 cytokine family which comprises IL-19 (Exemplary Human NCBI Reference Sequence: NP_715639.1), IL-20 (Exemplary Human NCBI Reference Sequence: NP_061194.2) and IL-24 (Exemplary Human NCBI Reference Sequence: NP_006841.1). IL-20 cytokines are very close to IL-22. IL-19 and IL-20 act via a receptor complex that consists of the IL-20R1 and IL-20R2 chains present on epithelial and antigen-presenting cells. IL-20 and IL-24 are additionally able to signal via a second receptor complex (IL-22R1/IL-20R2). Examples of human receptors for IL-20 cytokines include hIL-20R1 (also known as CRF2-8; IL-20RA; IL-20R-alpha) (Exemplary Human NCBI Reference Sequence: NP_055247.3), hIL-20R2 (also known as IL-20RB; IL-20R-beta) (Exemplary Human NCBI Reference Sequence: NP_653318.2) and hIL-22R1 (Exemplary NCBI Reference Sequence: NP_067081.2). More particularly, sequences of human receptors for IL-20 cytokines have been described; for example, in U.S. Pat. Nos. 6,610,286; 7,122,632; 7,393,684; and 7,537,761; and U.S. Pat. App. Pub. Nos. 2006/0263850 A1; 2006/0263851 A1; 2008/0247945 A1, and 2009/0074661 A1.

The "antagonist of IL-20 cytokines" to be used in the methods described herein is a molecule that blocks, suppresses, or reduces (including significantly) the biological activity of IL-20 cytokines, including downstream pathways mediated by signaling of IL-20 cytokines, such as receptor binding and/or elicitation of a cellular response to IL-20 cytokines. Thus the term "antagonist of IL-20 cytokines" implies no specific mechanism of biological action whatsoever, and is deemed to expressly include and encompass all possible pharmacological, physiological, and biochemical interactions with IL-20 cytokines and receptors whether direct or indirect. For purpose of the present disclosure, it will be explicitly understood that the term "antagonist of IL-20 cytokines" encompass all the previously identified terms, titles, and functional states and characteristics whereby the IL-20 cytokines themselves, a biological activity of IL-20 cytokines (including but not limited to its ability to control expression of IL-17 and IL-22 cytokines during acute exacerbation of COPD), or the consequences of the biological activity, are substantially nullified, decreased, or neutralized in any meaningful degree, e.g., by at least 20%, 50%, 70%, 85%, 90%, 100%, 150%, 200%, 300%, or 500%, or by 10-fold, 20-fold, 50-fold, 100-fold, 1000-fold, or $10^4$-fold.

Exemplary antagonists of IL-20 cytokines include, but are not limited to, an antibody directed against a IL-20 cytokine, an anti-sense nucleic acid molecule directed to an IL-20 cytokine (including an anti-sense nucleic acid directed to a nucleic acid encoding IL-20), a small interfering RNA (siRNA) directed toward an nucleic acid encoding for a IL-20 cytokine, a microRNA directed toward a nucleic acid encoding for a IL-20 cytokine, an anti-antibody directed against a receptor of a IL-20 cytokine (e.g., an antibody specifically binds IL-20R1, IL-20R2, IL-22RI or the dimeric complex formed thereby), an antisense nucleic acid molecule directed to a subunit of a receptor for a IL-20 cytokine, an siRNA or a microRNA directed to a nucleic acid encoding for a subunit of a receptor for a IL-20 cytokine.

In some embodiments, an antagonist of IL-20 cytokines binds to an IL-20 cytokine or a receptor and prevents the formation of the complex between the receptor and the cytokine, thereby inhibiting the signaling pathway. In some embodiments, an antagonist of IL-20 cytokines inhibits or reduces synthesis and/or production (release) of an IL-20 cytokine.

In some embodiments, the antagonist of IL-20 cytokines of the present invention is not an antibody directed against the IL-22R1 receptor, an anti-sense nucleic acid molecule directed toward an nucleic acid encoding for the IL-22R1, a small interfering RNA (siRNA) directed toward an nucleic acid encoding for a IL-22R1 receptor, a microRNA directed toward a nucleic acid encoding for a IL-22R1 receptor. In this manner, the signaling pathway of IL-22 is not disturbed.

In some embodiments, the antagonist of IL-20 cytokines is an antibody. For instance, the antibody disclosed herein specifically binds a target antigen, such as human IL-20 cytokine or one of the subunits of a human receptor for an IL-20 cytokine (e.g., IL-20R1). In some embodiments, the antagonist of IL-20 cytokines is selected from the group consisting of anti-IL-19 antibodies, anti-IL-20 antibodies, anti-IL-24 antibodies, anti-IL20R1 antibodies, and anti-IL20R2 antibodies.

An antibody that "specifically binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically (or preferentially) binds to an epitope is an antibody that binds this epitope with greater affinity, avidity, more readily, and/or with greater duration than it binds to other epitopes present in an IL-20 cytokine (or its receptor subunit) or epitopes that are not present in an IL-20 cytokine (or its receptor subunit). It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

The term "antibody" is thus used to refer to any antibody-like molecule that has an antigen binding region, and this term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art (see Kabat et al., 1991, specifically incorporated herein by reference). Diabodies, in particular, are further described in EP 404, 097 and WO 93/1 1 161; whereas linear antibodies are further described in Zapata et al. (1995). Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments.

In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs. In addition, determination of CDR regions in an antibody is well within the skill of the art. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Chothia et al. (1989) Nature 342:877; Al-lazikani et al (1997) J. Molec. Biol. 273:927-948)). As used herein, a CDR may refer to CDRs defined by either approach or by a combination of both approaches.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with the relevant antigenic forms (e.g. an IL-20 cytokine or a receptor). The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes.

Briefly, the recombinant antigen (e.g. an IL-20 cytokine or a receptor) may be provided by expression with recombinant cell lines. For instance receptors (e.g. IL-20R1 or IL-20R2) may be provided in the form of human cells expressing the receptor at their surface. Recombinant forms of the cytokine or receptor may be provided using any previously described method. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods, as described (Coding, Monoclonal Antibodies: Principles and Practice: Production and Application of Monoclonal Antibodies in Cell Biology, Biochemistry and Immunology, 3rd edition, Academic Press, New York, 1996). Following culture of the hybridomas, cell supernatants are analyzed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology,* 7th Ed., Blackwell Scientific Publications, Oxford). The Fc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR5). The CDRs, and in particular the CDR5 regions, and more particularly the heavy chain CDR5, are largely responsible for antibody specificity.

It is now well-established in the art that the non CDR regions of a mammalian antibody may be replaced with similar regions of specific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody.

In some embodiments, the antibody is a humanized antibody. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference. The above U.S. Pat. Nos. 5,585,089 and 5,693,761, and WO 90/07861 also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3 A of the CDRs in a three dimensional model of the antibody and is predicted to be capable of interacting with the CDRs. The above methods are merely illustrative of some of the methods that one skilled in the art could employ to make humanized antibodies. One of ordinary skill in the art will be familiar with other methods for antibody humanization.

In some embodiments, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody retains a similar antigenic specificity as the original antibody. However, using certain methods of humanization, the affinity and/or specificity of binding of the antibody may be increased using methods of "directed evolution", as described by Wu et al., *I. Mol. Biol.* 294:151, 1999, the contents of which are incorporated herein by reference.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/Gen- Pharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans. In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

Thus, as will be apparent to one of ordinary skill in the art, the present invention also provides for F(ab') 2 Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The various antibody molecules and fragments may derive from any of the commonly known immunoglobulin classes, including but not limited to IgA, secretory IgA, IgE, IgG and IgM. IgG subclasses are also well known to those in the art and include but are not limited to human IgG1, IgG2, IgG3 and IgG4.

The binding affinity of an antibody can be less than any of about 100 nM, about 50 nM, about 10 nM, about 1 nM, about 500 pM, about 100 pM, or about 50 pM to any of about 2 pM. Binding affinity can be expressed KD or dissociation constant, and an increased binding affinity corresponds to a decreased KD. One way of determining binding affinity of antibodies is by measuring binding affinity of monofunctional Fab fragments of the antibody. To obtain monofunctional Fab fragments, an antibody (for example, IgG) can be cleaved with papain or expressed recombinantly. The affinity of an anti-IL-20 Fab fragment of an antibody can be determined by surface plasmon resonance (BIAcore3000™ surface plasmon resonance (SPR) system, BlAcore, INC, Piscaway N.J.). Kinetic association rates (kon) and dissociation rates (koff) (generally measured at 25° C.) are obtained; and equilibrium dissociation constant (KD) values are calculated as koff/kon.

Examples of anti-IL-20 antibodies include, but are not limited to, those disclosed in U.S. Pat. Nos. 7,435,800; 7,115,714; 7,119,175; 7,151,166; and 7,393,684; and PCT publications WO 2007/081465; WO 99/27103; WO 2004/085475; and WO 2005052000. In some embodiments, the anti-IL-20 antibody described herein is anti-IL-20 antibody 7E, which refers to monoclonal antibody mAb 7E and its functional variants. MAb 7E is produced by the hybridoma cell line deposited at the American Type Culture Collection, 10801 University Boulevard, Manassas, Va. 20110-2209, U.S.A. and assigned a deposit number PTA-8687. This hybridoma cell line will be released to the public irrevocably and without restriction/condition upon granting a US patent on this application, and will be maintained in the ATCC for a period of at least 30 years from the date of the deposit for the enforceable life of the patent or for a period of 5 years after the date of the most recent. A functional variant (equivalent) of mAb7E has essentially the same epitope-binding specificity as mAb7E and exhibits at least 20% (e.g., 30%, 40%, 50%, 60%, 70%, 80%, 90%, or greater) of the activity of neutralizing a signaling pathway mediated by IL-20 as relative to mAb7E. In some embodiments, a functional variant of mAb7E contains the same regions/residues responsible for antigen-binding as mAb7E, such as the same specificity-determining residues in the CDRs or the whole CDRs. The regions/residues that are responsible for antigen-binding can be identified from amino acid sequences of the heavy chain/light chain sequences of mAb7GW or mAb51D (shown above) by methods known in the art. See, e.g., www.bioinf.org.uk/abs; Almagro, J. Mol. Recognit. 17:132-143 (2004); and Chothia et al., J. Mol. Biol. 227: 799-817 (1987).

In some embodiments, the anti-IL20R1 antibody used in the methods described herein is an antibody having the same heavy chain and light chain variable regions (VH and VL) as those of monoclonal antibody mAb7GW or mAb51D, the monoclonal antibodies, an antigen-binding fragment thereof, or a functional equivalent of either mAb7GW or mAb51D disclosed in US2011/0256093, which is herein incorporated by reference in its entirety. A functional equivalent of mAb7GW or mAb51D has the same epitope-binding specificity as mAb7GW or mAb51D and exhibits at least 20% (e.g., 30%, 40%, 50%, 60%, 70%, 80%, 90%, or greater) of the activity of neutralizing a signaling pathway mediated by IL-20R1 as relative to mAb7GW or mAb51D. In some embodiments, a functional equivalent of mAb7GW or mAb51D contains the same regions/residues responsible for antigen-binding as mAb7GW or mAb51D, such as the same specificity-determining residues in the CDRs or the whole CDRs. The regions/residues that are responsible for antigen-binding can be identified from amino acid sequences of the heavy chain/light chain sequences of mAb7GW or mAb51D (shown above) by methods known in the art. See, e.g., www.bioinf.org.uk/abs; Almagro, J. Mol. Recognit. 17:132-143 (2004); and Chothia et al., J. Mol. Biol. 227: 799-817 (1987).

In some embodiments, the antagonist of IL-20 cytokines is polypeptide. In some embodiments, polypeptide comprises a functional equivalent of an IL-20 receptor (i.e. IL-20R1, IL-20R2, and IL-22RI). As used herein, a "functional equivalent of an IL-20 receptor" is a polypeptide which is capable of binding to an IL-20 cytokine, thereby preventing its interaction with an IL-20 receptor. The term "functional equivalent" includes fragments, mutants, and muteins of IL-20 receptor. The term "functionally equivalent" thus includes any equivalent of an IL-20 receptor obtained by altering the amino acid sequence, for example by one or more amino acid deletions, substitutions or additions such that the protein analogue retains the ability to bind to an IL-20 cytokine. Amino acid substitutions may be made, for example, by point mutation of the DNA encoding the amino acid sequence. Functional equivalents include molecules that bind an IL-20 cytokine and comprise all or a portion of the extracellular domains of IL-20 receptor so as to form a soluble receptor that is capable to trap the IL-20 cytokine. Thus the functional equivalents include soluble forms of the IL-20 receptor. A suitable soluble form of these proteins, or functional equivalents thereof, might comprise, for example, a truncated form of the protein from which the transmembrane domain has been removed by chemical, proteolytic or recombinant methods. Typically, the functional equivalent is at least 80% homologous to the corresponding protein. In a preferred embodiment, the functional equivalent is at least 90% homologous as assessed by any conventional analysis algorithm. The term "a functionally equivalent fragment" as used herein also may mean any fragment or assembly of fragments of IL-20 receptor that binds to an IL-20 cytokine. Accordingly the present invention provides a polypeptide capable of inhibiting binding of an IL-20 receptor to an IL-20 cytokine, which polypeptide comprises consecutive amino acids having a sequence which corresponds to the sequence of at least a portion of an extracellular domain of an IL-20 receptor, which portion binds to an IL-20 cytokine. In some embodiments, the polypeptide corresponds to an extracellular domain of an IL-20 receptor. In some embodiments, the polypeptide does not comprise a functional equivalent of IL-22RI.

In some embodiments, the polypeptide comprises a functional equivalent of an IL-20 receptor which is fused to an immunoglobulin constant domain (Fc region) to form an immunoadhesin. Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use. In some embodiments, the Fc region is a native sequence Fc region. In some embodiments, the Fc region is a variant Fc region. In still another embodiment, the Fc region is a functional Fc region. As used herein, the term "Fc region" is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The adhesion portion and the immunoglobulin sequence portion of the immunoadhesin may be linked by a minimal linker. The immunoglobulin sequence typically, but not necessarily, is an immunoglobulin constant domain. The immunoglobulin moiety in the chimeras of the present invention may be obtained from IgG1, IgG2, IgG3 or IgG4 subtypes, IgA, IgE, IgD or IgM, but typically IgG1 or IgG3. In some embodiments, the functional equivalent of the IL-20 receptor and the immunoglobulin sequence portion of the immunoadhesin are linked by a minimal linker. As used herein, the term "linker" refers to a sequence of at least one amino acid that links the polypeptide of the invention and the immunoglobulin sequence portion. Such a linker may be useful to prevent steric hindrances. In some embodiments, the linker has 4; 5; 6; 7; 8; 9; 10; 11; 12; 13; 14; 15; 16; 17; 18; 19; 20; 21; 22; 23; 24; 25; 26; 27; 28; 29; 30 amino acid residues. However, the upper limit is not critical but is chosen for reasons of convenience regarding e.g. biopharmaceutical production of such polypeptides. The linker sequence may be a naturally occurring sequence or a non-naturally occurring sequence. If used for therapeutical purposes, the linker is typically non-immunogenic in the subject to which the immunoadhesin is administered. One useful group of linker sequences are linkers derived from the hinge region of heavy chain antibodies as described in WO 96/34103 and WO 94/04678. Other examples are poly-alanine linker sequences.

In some embodiments, the polypeptide comprises the extracellular domain of the IL-20R1 polypeptide and the extracellular domain of the IL-20RII which are covalently linked together. In some embodiments one extracellular domain has a constant region of a heavy chain of an immunoglobulin fused to its carboxy terminus and the other extracellular domain has a constant light chain of an immunoglobulin (Ig) fused to its carboxy terminus such that the two polypeptides come together to form a soluble receptor and a disulfide bond is formed between the heavy and the light Ig chains. In some embodiments, a peptide linker could be fused to the two carboxy-termini of the extracellular domains to form a covalently bonded soluble receptor.

The polypeptides of the invention may be produced by any suitable means, as will be apparent to those of skill in the art. In order to produce sufficient amounts of IL-20 receptor or functional equivalents thereof for use in accordance with the present invention, expression may conveniently be achieved by culturing under appropriate conditions recombinant host cells containing the polypeptide of the invention. Typically, the polypeptide is produced by recombinant means, by expression from an encoding nucleic acid molecule. Systems for cloning and expression of a polypeptide in a variety of different host cells are well known. When expressed in recombinant form, the polypeptide is typically generated by expression from an encoding nucleic acid in a host cell. Any host cell may be used, depending upon the individual requirements of a particular system. Suitable host cells include bacteria mammalian cells, plant cells, yeast and baculovirus systems. Mammalian cell lines available in the art for expression of a heterologous polypeptide include Chinese hamster ovary cells. HeLa cells, baby hamster kidney cells and many others. Bacteria are also preferred hosts for the production of recombinant protein, due to the ease with which bacteria may be manipulated and grown. A common, preferred bacterial host is *E coli*.

In some embodiments, it is contemplated that polypeptides used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution. In example adding dipeptides can improve the penetration of a circulating agent in the eye through the blood retinal barrier by using endogenous transporters. A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain. Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications. Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 60 kDa). In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes. Such linkers may be used in modifying the protein or fragment of the protein described herein for therapeutic delivery.

In some embodiments, the antagonist of IL-20 cytokines is an inhibitor of expression. An "inhibitor of expression" refers to a natural or synthetic compound that has a biological effect to inhibit the expression of a gene (i.e. IL-19, IL-20, IL-24, IL-20R1 or IL-20R2). In some embodiments, said inhibitor of gene expression is a siRNA, an antisense oligonucleotide or a ribozyme. For example, anti-sense oligonucleotides, including anti-sense RNA molecules and anti-sense DNA molecules, would act to directly block the translation of RIP2 mRNA by binding thereto and thus preventing protein translation or increasing mRNA degradation, thus decreasing the level of an IL-20 cytokine or a receptor subunit thereof, and thus activity, in a cell. For example, antisense oligonucleotides of at least about 15 bases and complementary to unique regions of the mRNA transcript sequence encoding RIP2 can be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Small inhibitory RNAs (siRNAs) can also function as inhibitors of expression for use in the present invention. Gene expression can be reduced by contacting a subject or cell with a small double stranded RNA (dsRNA), or a vector or construct causing the production of a small double stranded RNA, such that gene expression is specifically inhibited (i.e. RNA interference or RNAi). Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and typically cells expressing RIP2. Typically, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

By a "therapeutically effective amount" is meant a sufficient amount of the polypeptide (or the nucleic acid encoding for the polypeptide) to prevent for use in a method for the treatment of acute exacerbation of COPD at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, typically from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Typically the active ingredient of the present invention (i.e. the antagonist of IL-20 cytokines) is combined with pharmaceutically acceptable excipients, and optionally sustained-release matrices, such as biodegradable polymers, to form pharmaceutical compositions. The term "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. In the pharmaceutical compositions of the present invention, the active ingredients of the invention can be administered in a unit administration form, as a mixture with conventional pharmaceutical supports. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

In some embodiment, the antagonist of IL-20 cytokines is administered to the subject in combination with an antibacterial agent, such as antibiotics or antiviral agents. Suitable antibiotics that could be coadministered in combination with the antagonist include, but are not limited to, at least one antibiotic selected from the group consisting of: ceftriaxone, cefotaxime, vancomycin, meropenem, cefepime, ceftazidime, cefuroxime, nafcillin, oxacillin, ampicillin, ticarcillin, ticarcillin/clavulinic acid (Timentin), ampicillin/sulbactam (Unasyn), azithromycin, trimethoprim-sulfamethoxazole, clindamycin, ciprofloxacin, levofloxacin, synercid, amoxicillin, amoxicillin/clavulinic acid (Augmentin), cefuroxime,trimethoprim/sulfamethoxazole, azithromycin, clindamycin, dicloxacillin, ciprofloxacin, levofloxacin, cefixime, cefpodoxime, loracarbef, cefadroxil, cefabutin, cefdinir, and cephradine. Example of antiviral agents include but are not limited to acyclovir, famciclovir, valaciclovir, ganciclovir, cidofovir; amantadine, rimantadine; ribavirin; zanamavir and/or oseltamavir; a protease inhibitor, such as indinavir, nelfinavir, ritonavir and/or saquinavir; a nucleoside reverse transcriptase inhibitor, such as didanosine, lamivudine, stavudine, zalcitabine, zidovudine; a nonnucleoside reverse transcriptase inhibitor, such as nevirapine, efavirenz.

Combination treatment may also include respiratory stimulants. Corticosteroids may be beneficial in acute exacerbations of COPD. Examples of corticosteroids that can be used in combination with the antagonist of the present invention are prednisolone, methylprednisolone, dexamethasone, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone farnesylate, ciclesonide, deprodone propionate, fluticasone propionate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate and hydrocortisone probutate. Particularly preferred corticosteroids under the present invention are: dexamethasone, budesonide, beclomethasone, triamcinolone, mometasone, ciclesonide, fluticasone, flunisolide, dexamethasone sodium phosphate and esters thereof as well as 6α,9α-difluoro-17α-[(2-furanylcarbonyl)oxy]-11β-hydroxy-16α-methyl-3-oxoandrosta-1,4-diene-17β-carbothioic acid (S)-fluoromethyl ester. Still more preferred corticosteroids under the present invention are: budesonide, beclomethasone dipropionate, mometasone furoate, ciclesonide, triamcinolone, triamcinolone acetonide, triamcinolone hexaacetonide and fluticasone propionate optionally in the form of their racemates, their enantiomers, their diastereomers and mixtures thereof, and optionally their pharmacologically-compatible acid addition salts. Even more preferred are budesonide, beclomethasone dipropionate, mometasone furoate, ciclesonide and fluticasone propionate. The most preferred corticosteroids of the present invention are budesonide and beclomethasone dipropionate.

Bronchodilator dosages may be increased during acute exacerbations to decrease acute bronchospasm. Examples of bronchodilators include but are not limited to β2-agonists (e.g. salbutamol, bitolterol mesylate, formoterol, isoproterenol, levalbuterol, metaproterenol, salmeterol, terbutaline, and fenoterol), anticholinergic (e.g. tiotropium or ipratropium), methylxanthined, and phosphodiesterase inhibitors.

In some embodiments, the antagonist of the invention is administered to the subject in combination with a vaccine which contains an antigen or antigenic composition capable of eliciting an immune response against a virus or a bacterium. Typically, the vaccine composition is used to eliciting an immune response against at least one bacterium selected from the group consisting of *Streptococcus pneumoniae, Staphylococcus aureus, Burkholderis* ssp., *Streptococcus agalactiae, Haemophilus influenzae, Haemophilus parainfluenzae, Klebsiella pneumoniae, Escherichia coli, Pseudomonas aeruginosa, Moraxella catarrhalis, Chlamydophila pneumoniae, Mycoplasma pneumoniae, Legionella pneumophila, Serratia marcescens, Mycobacterium tuberculosis, Bordetella pertussis*. In particular, the vaccine composition is directed against *Streptococcus pneumonia* or *Haemophilus influenza*. More particularly, the vaccine composition is directed against Non-typeable *Haemophilus influenzae* (NTHi). Typically, vaccine composition typically contains whole killed or inactivated (eg., attenuated) bacteria isolate(s). However, soluble or particulate antigen comprising or consisting of outer cell membrane and/or surface antigens can be suitable as well, or instead of, whole killed organisms. In one or more embodiments, the outer cellular membrane fraction or membrane protein(s) of the selected isolate(s) is used. For instance, NTHi OMP P6 is a highly conserved 16-kDa lipoprotein (Nelson, 1988) which is a target of human bactericidal antibody and induces protection both in humans and in animal models. In chronic pulmonary obstructive disease (COPD), OMP P6 has been shown to evoke a lymphocyte proliferative response that is associated with relative protection from NTHi infection (Abe, 2002). Accordingly, OMP P6 or any other suitable outer membrane NTHi proteins, polypeptides (eg., P2, P4 and P26) or antigenic fragments of such proteins or polypeptides can find application for a NTHi vaccine. Soluble and/or particulate antigen can be prepared by disrupting killed or viable selected isolate(s). A fraction for use in the vaccine can then be prepared by centrifugation, filtration and/or other appropriate techniques known in the art. Any method which achieves the required level of cellular disruption can be employed including sonication or dissolution utilizing appropriate surfactants and agitation, and combination of such techniques. When sonication is employed, the isolate can be subjected to a number of sonication steps in order to obtain the required degree of cellular disruption or generation of soluble and/or particulate matter of a specific size or size range. In some embodiments, the vaccine composition comprises an adjuvant, in a particular TLR agonist. In one embodiment, the TLR agonist is selected from the group consisting of TLR1, TLR2, TLR3, TLR4, TLR5, TLR6, TLR7, TLR8, TLR9, TLR10, TLR11, TLR12, or TLR13 agonists.

In certain embodiments, oxygen requirements may increase and supplemental oxygen may be provided.

The invention will be further illustrated by the following figures and examples. However, these examples and figures should not be interpreted in any way as limiting the scope of the present invention.

FIGURES

FIG. 1—COPD patients have a defective response to *Streptococcus pneumoniae* (Sp). Production of IL-17 and IL-22 was evaluated by ELISA in supernatants from mononuclear cells from not smoker healthy subjects (controls), smokers healthy subjects and COPD patients. Results were expressed as mean±SEM. *: p<0.05 vs controls.

Figure 2:
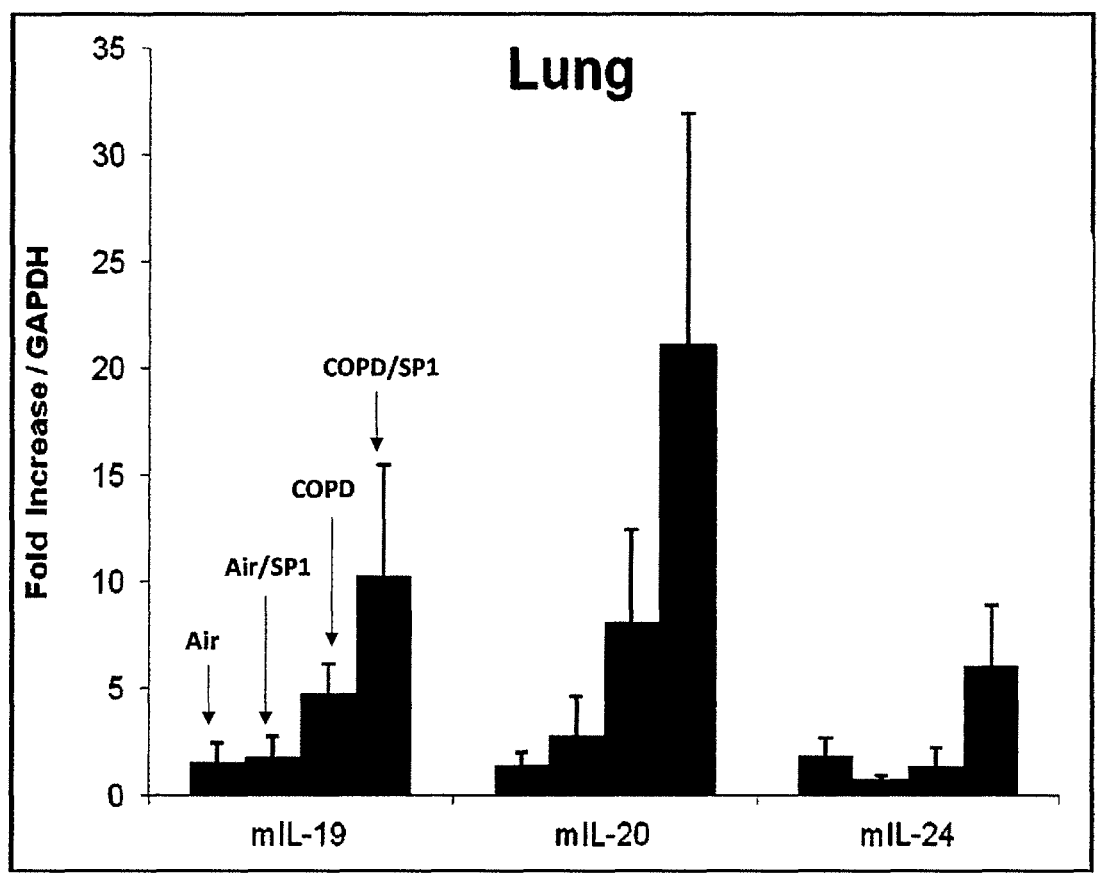

FIG. 2: The expression of IL-19, IL-20 and IL-24 was induced by exposure to cigarette smoke (CS) and by infection with *S. pneumoniae* (SP) with an additive effect between both stimuli in the lung of wild type mice.

Figure 3:
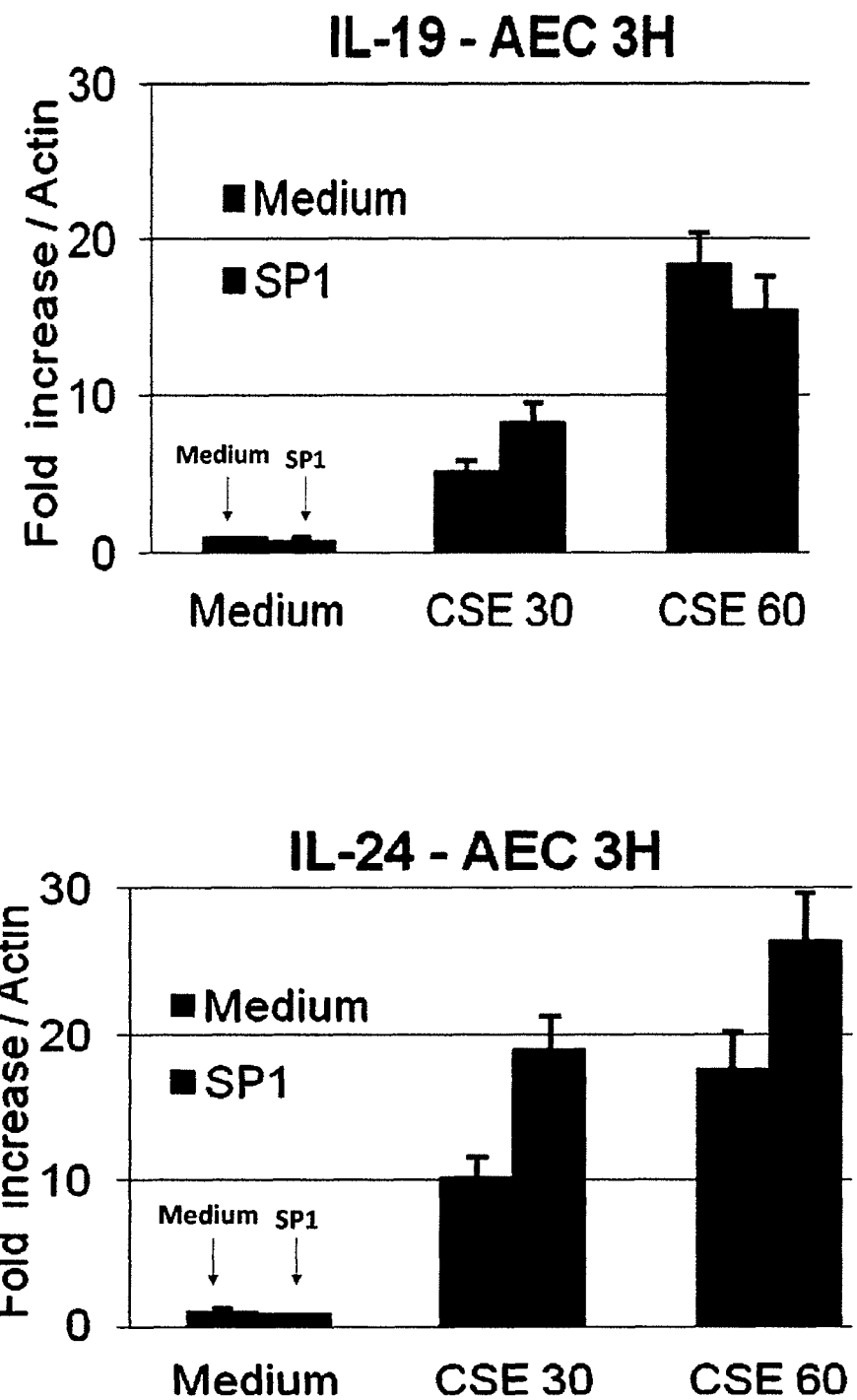

FIG. 3: The mRNA expression of IL-19 and IL-24 in the human airway epithelial cells (AEC) BEAS-2B cells, was induced by exposure to CS extract (CSE) but not by infection with *S. pneumoniae* (SP1). CSE was added either at 1/30 or 1/60 dilution (CSE30 vs CSE60).

Figure 4:
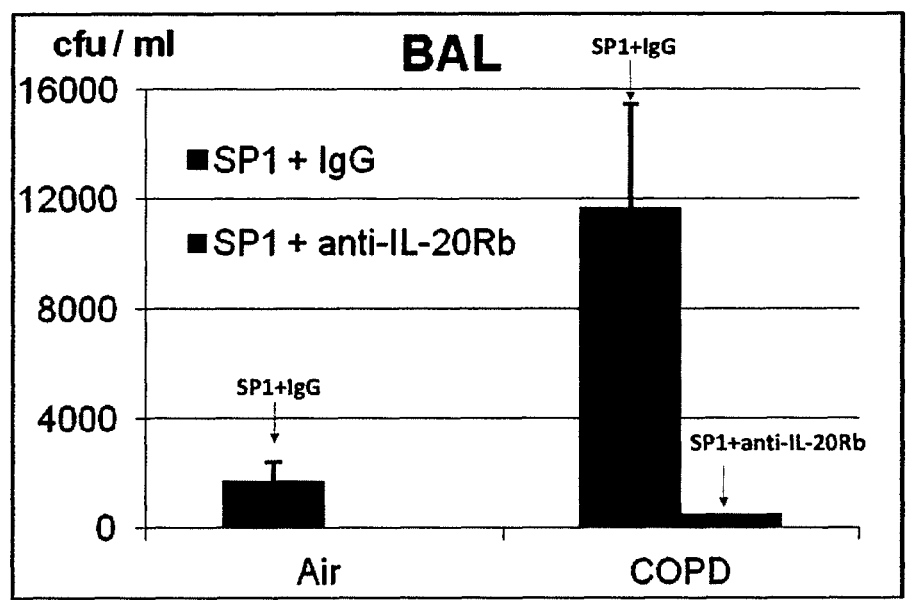
Figure 4:
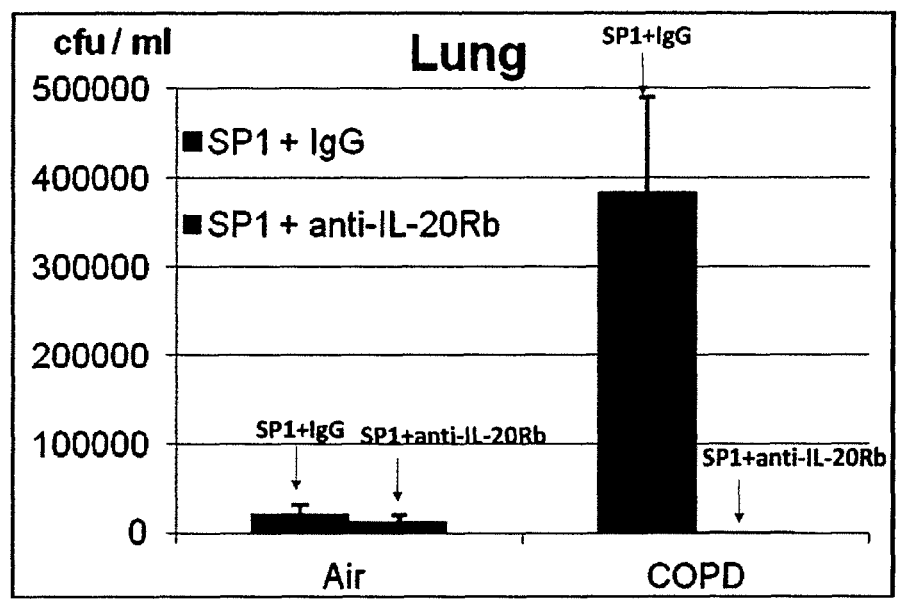

FIG. 4: The bacterial load was measured in Bronchoalveaolar lavage (BAL) and lung lysates from COPD mice infected with *S. pneumoniae* (SP1) and treated with either the isotype control (IgG) or anti-IL-20Rβ antibody. BAL and lungs were collected at day 3 after infection.

Figure 5:
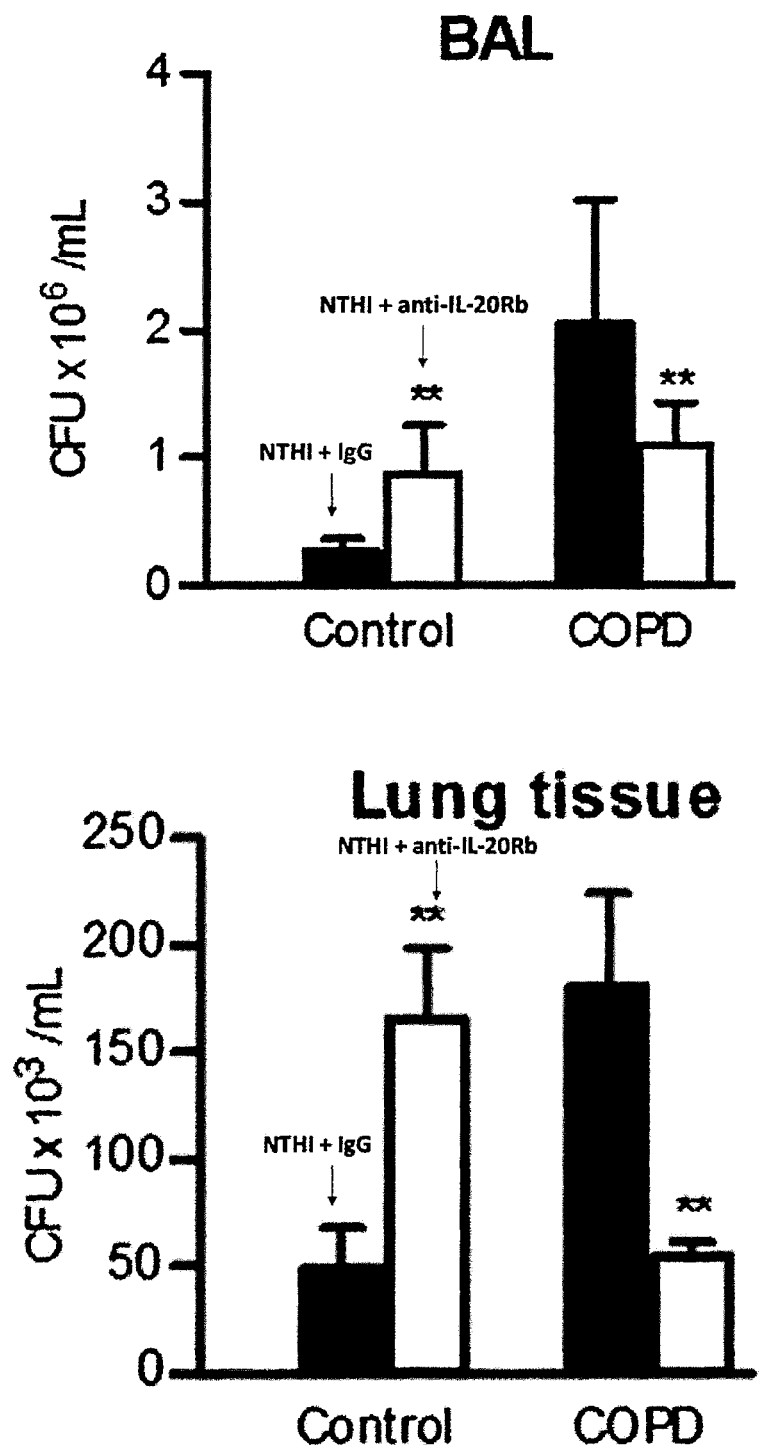

FIG. 5: The bacterial load was measured in Bronchoalveaolar lavage (BAL) and lung lysates from COPD mice infected with not typable *Haemophilus influenza* (NTHi) and treated with either the isotype control (IgG) or anti-IL-20Rβ antibody. BAL and lungs were collected at day 1 after infection. **: p<0.01 as compared with infected mice exposed to air or to CS (COPD), respectively.

Figure 6:
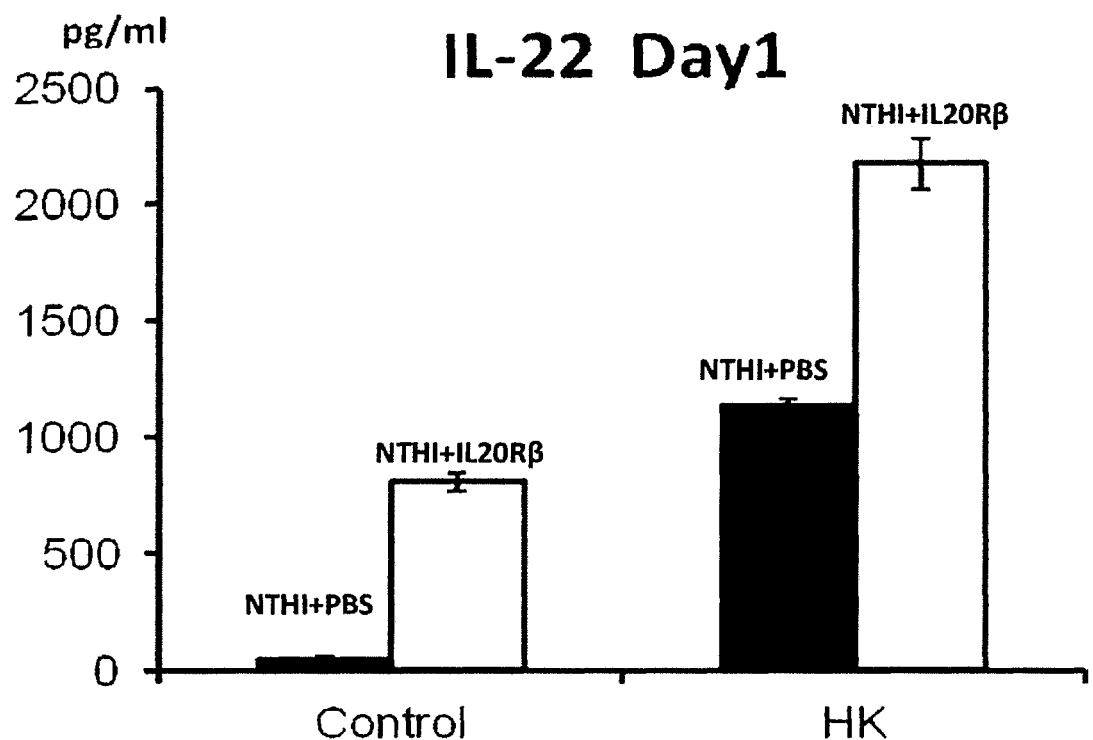
Figure 6:
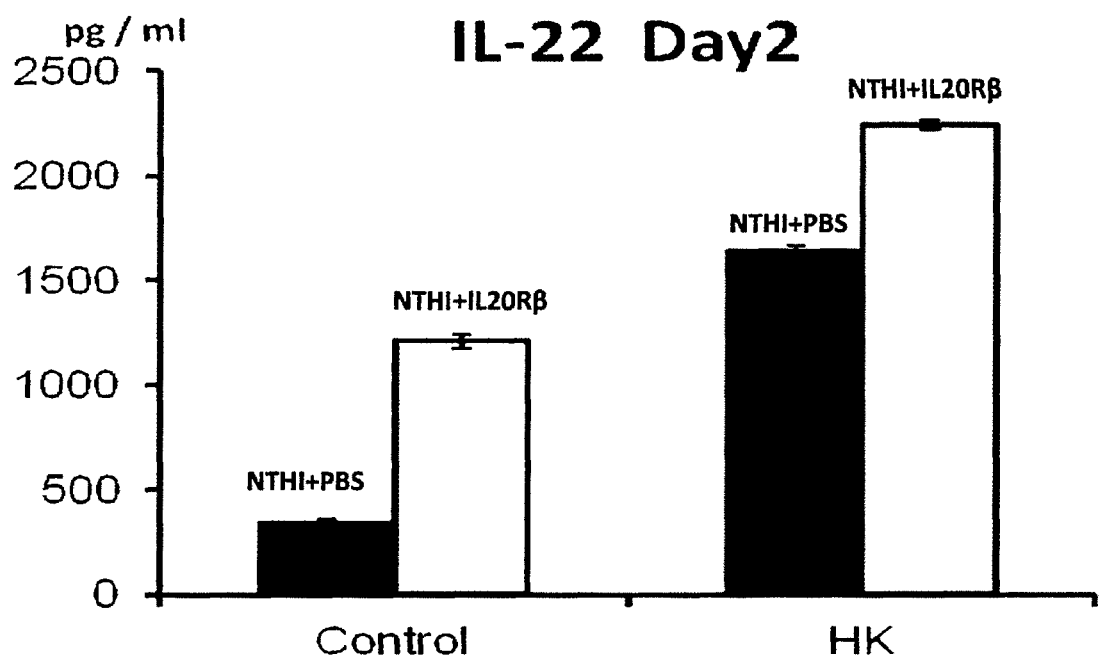

FIG. 6: The secretion of IL-22 was measured in lung cells from COPD mice infected with not typeable *H. influenza* (NTHI) and treated with either the isotype control (NTHI+ PBS) or anti-IL-20Rβ antibody. Lung cells were collected either at day 1 and 2 after infection and incubated for 3 days at 37° C. in medium alone or in presence of heat-killed bacteria (HK).

Figure 7:
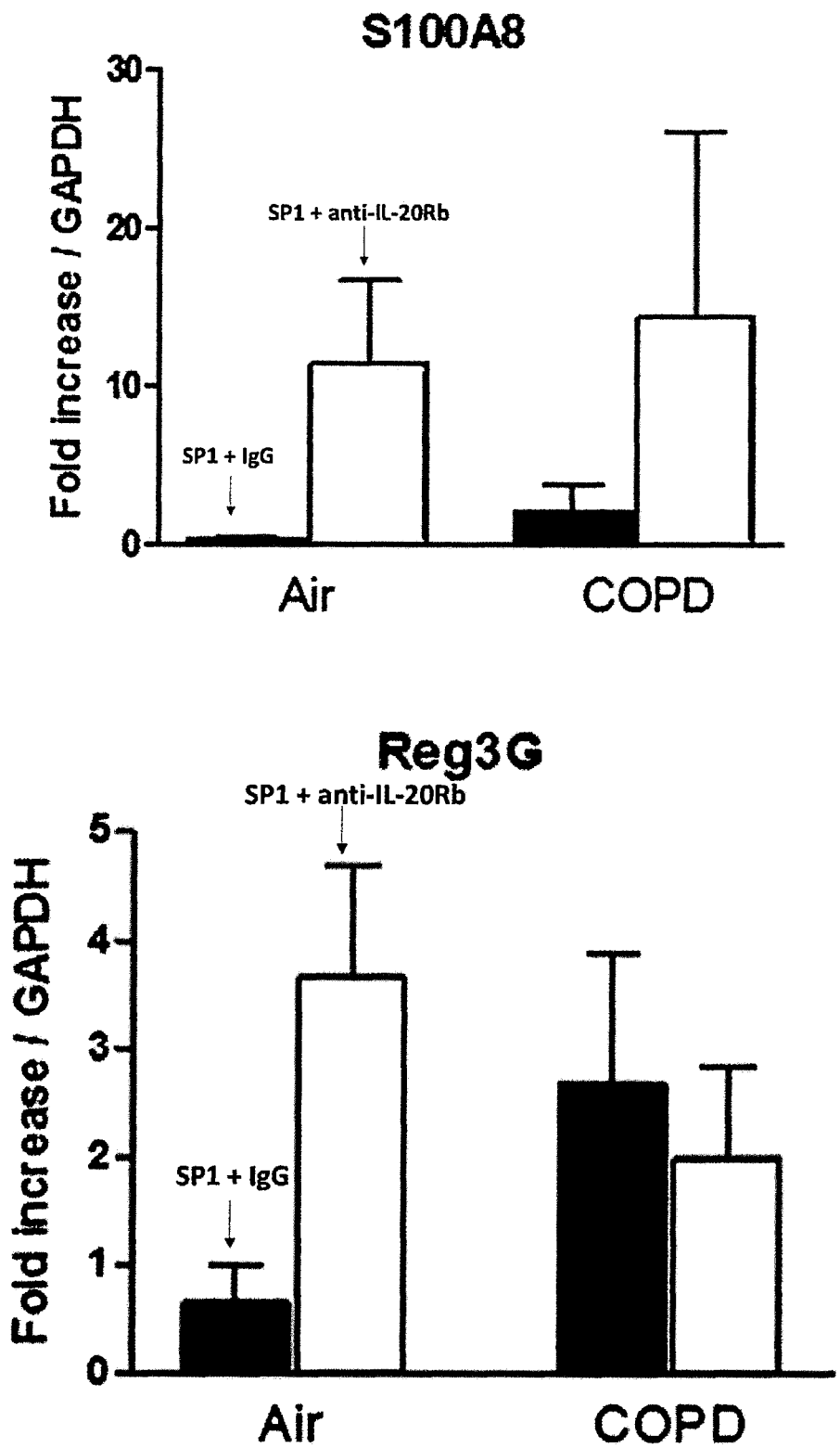

FIG. 7: Expression of the mRNA encoding for the antimicrobial peptides S100A8 and REG3G in the lung tissue from COPD mice infected with *S. pneumoniae* (Sp1) and treated with either the isotype control (IgG) or anti-IL-20Rβ antibody. Lungs were collected at day 3 after infection.

Figure 8:
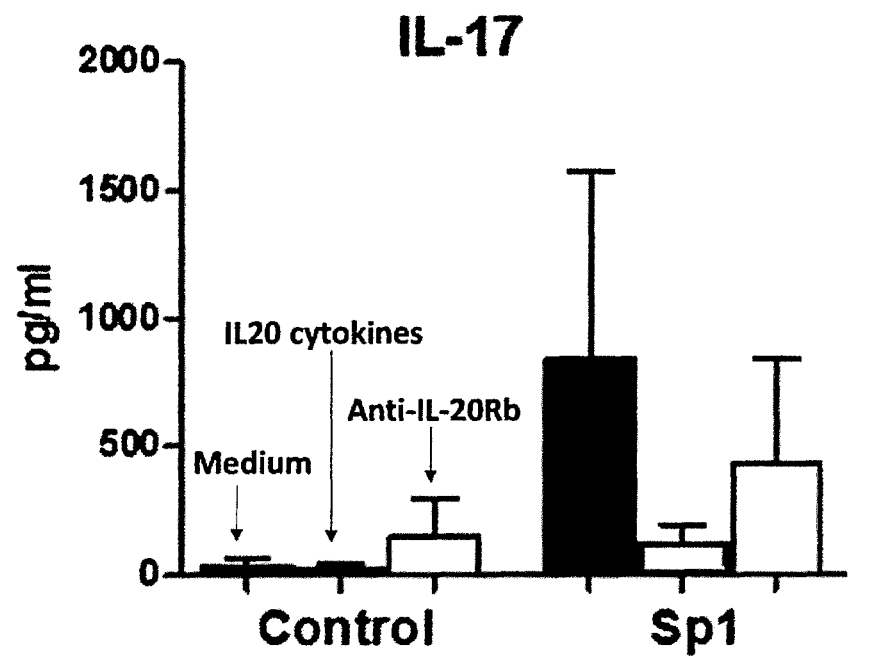
Figure 8:
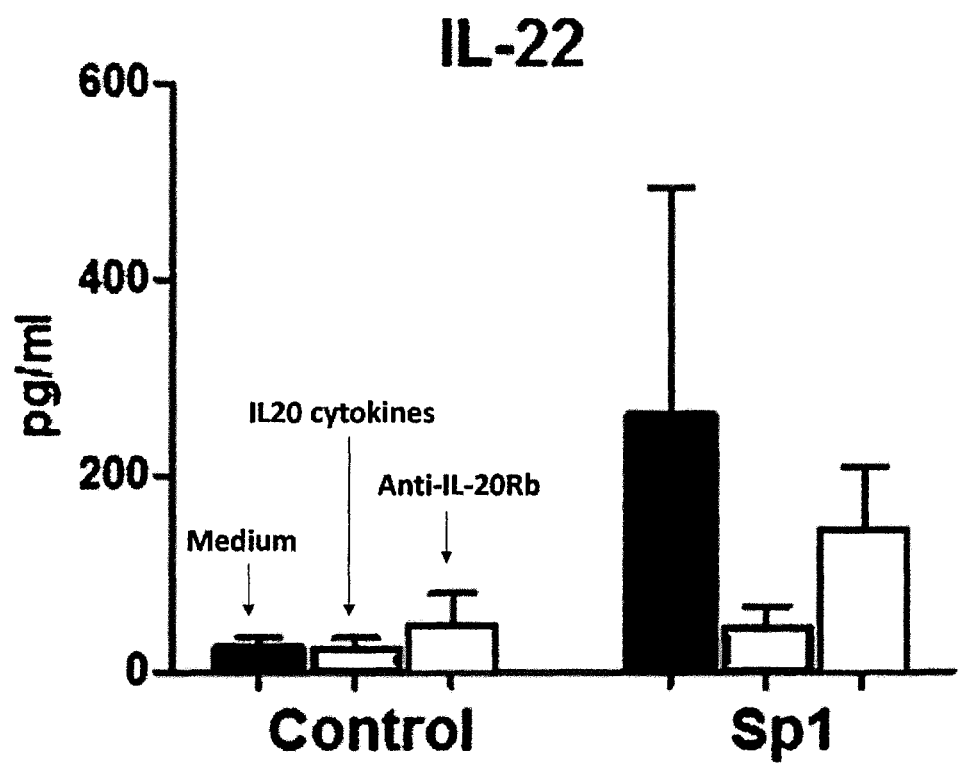

FIG. 8: Treatment with IL-20 cytokines and anti-IL-20Rβ antibody modulated in a different manner the ability of monocyte-derived dendritic cell (MDDC) to prime IL-17 and IL-22 production by T cells in response to activation by *S. pneumoniae* (Sp1).

EXAMPLE

Introduction: Bacterial complications are a common feature during a wide variety of lung inflammatory disorders such as COPD. In patients with COPD, acute exacerbation is mostly associated with bacterial infections frequently due to *Haemophilus influenzae* and *Streptococcus pneumoniae*. These infections provoked a strong inflammatory reaction characterized by neutrophil recruitment, increased production of pro-inflammatory cytokines and accelerated the progression of the disease. Appropriate models are needed to better define mechanisms responsible for bacterial susceptibility during the exacerbation of COPD. We have already developed a murine model of COPD by chronic exposure to cigarette smoke (CS) during 12 weeks. This exposure strongly modifies the innate immune response in the lung and the activation of invariant natural killer T (iNKT) cells (Pichavant M et al., Mucosal Immunol, 2014). To better define the mechanisms responsible for bacterial susceptibility, we have now developed experimental models of COPD exacerbation in C57/BL6 mice chronically exposed to CS and then, infected by the local administration of sub-lethal doses of *H. influenzae* and *S. pneumoniae*.

IL-17 and IL-22 response to bacterial infection is altered in COPD mice: Infected COPD mice develop a strong lung infection with SP (associated with an increased inflammatory reaction) whereas naïve mice are able to clear the bacteria within 24 hours. This defect in bacterial clearance is associated with a lower production of both IL-17 and IL-22 in the BAL and after restimulation of lung cells. The defect in IL-17 and IL-22 is related to a decreased percentage of NK, NKT cells as well as innate lymphoid cells (ILC) positive for these cytokines in the lung of infected COPD mice as compared to infected air-exposed mice. Moreover, the supplementation with recombinant IL-22 allows to accelerate the clearance of the bacteria and to limit the consequences of the infection by *S. pneumoniae* in COPD mice. In COPD mice, infection with *H. influenzae* is associated with a defect in the production of IL-22 which also involved the same cells as observed for SP (ILC, NK and NKT cells). Since the role of IL-22 is unknown during infection by *H. influenzae*, we observed that IL-22-/mice reproduce a phenotype close to that of COPD mice (increased susceptibility, higher inflammatory response and lung remodeling). These data show that COPD mice are more susceptible to infection by *H. influenzae* and *S. pneumoniae* than control mice and a deficient production of IL-17 and/or IL-22 may favor the development of bacteria-induced COPD exacerbations.

IL-17 and IL-22 response to bacterial infection is altered in mononuclear cells from COPD patients: Although a defect in the production of IL-17 and IL-22 might play a role in the susceptibility to bacterial infection during COPD, there is no data reporting the concentrations of these cytokines in the lung from patients with AE-COPD. In order to estimate the capacity of COPD patients to produce Th17 cytokines in response to bacteria, we first analyze the response to *S. pneumoniae* of blood mononuclear cells (MNC) from COPD patients in comparison with healthy smokers and not smokers. A positive control of MNC activation was also included by addition of phytohemagglutinin (PHA). The concentrations of cytokines in unstimulated cells were not significantly different among the 3 groups (FIG. 1). Whereas both stimuli significantly increased the levels of IL-17 and IL-22 in not smokers (controls) and smokers, the exposure to Sp did not significantly amplify the secretion of these cytokines in COPD patients. The response to PHA was also partially altered in COPD patients, mainly for IL-17 and IL-22. In order to identify the cell sources for these cytokines in response to *S. pneumoniae*, we analysed the intracellular staining for IL-17 and IL-22 in these MNC. As compared with smokers and not smokers, the production of IL-17 and IL-22 was altered in Lin- (potentially the ILC), iNKT and NK cells but not in Tγε cells from COPD patients (data not shown).

Production of IL-20 cytokines after exposure to cigarette smoke and in response to bacterial infection: Since IL-20 cytokines are related to IL-22 and their production is induced by some bacteria (*Staphylococcus Aureus*), we evaluated the expression of these cytokines in our experimental models. After chronic exposure to CS, the expression of IL-19 and IL-20 mRNA was increased in the lung of COPD mice as compared to controls (air-exposed animals) (FIG. 2). In addition, air mice infected with *S. pneumoniae* did not produce IL-19 and IL-24 whereas IL-20 mRNA expression was upregulated. In COPD mice, infection with *S. pneumoniae* markedly enhanced the expression of IL-19, 1L-20 and IL-24 even we compared the results to the not-infected COPD mice.

Similar results were obtained after infection with not typeable *H. influenzae* (NTHI), namely, an additive effect of CS exposure and bacterial infection on the expression of these cytokines.

We also analyzed the expression of these cytokines in human dendritic cells (DC) and airway epithelial cells (AEC) activated in vitro by CS extract (CSE) and/or bacteria. As reported in FIG. 3, infection with SP1 did not significantly increased the expression of IL-19 and IL-24. In contrast, exposure to CSE had a strong effect on both cytokines alone or in presence of *S. pneumoniae*. Similar results were obtained with monocyte-derived DC (data not shown).

Function of IL-20 cytokines in response to bacterial infection during COPD: Since Myles IA et al (Nat Immunol. 2013) reported that signaling via the IL-20 receptor inhibits the production of IL-17 and IL-22 to promote cutaneous infection, we hypothesized that these receptors were implicated in the defect in IL-17 and IL-22 response observed in bacterial infection of COPD mice. To demonstrate this, we used a neutralizing antibody that recognize the IL-20Rβ subunit. This receptor is common to both receptors binding IL-19, IL-20 or IL-24 (IL-20Rα/IL-20Rβ, IL-22Rα/IL-20Rβ). This commercially available antibody anti-IL-20Rβ (clone 20RNTC, which recognized both human and mouse) is intraperitoneally administered one day before the infection and the day after (50 μg/injection/mouse). For these preliminary experiments, we analyzed the bacterial load and the expression of Th17 cytokines.

As illustrated in FIG. 4, treatment with blocking anti-IL-20Rβ antibodies strongly decreased the bacterial load in the BAL and the lung tissue after infection with *S. pneumoniae*. Similar results were obtained after infection with *H. influenzae* (data not shown). In contrast, this treatment had a moderate or no effect in Air infected mice suggesting that the activity of this antibody is related to the expression level of the IL-20R ligands.

In parallel, we evaluated the expression of Th17 cytokines in the lungs of infected COPD mice. As illustrated in FIG. 5, an increased secretion of IL-22 was detected in lung cells from COPD mice treated with anti-IL-20Rb antibody as compared to the mice receiving the isotype control, whatever at day 1 and 2 after infection with NTHI.

Conclusion: Altogether, these data underlines the interest of antagonist of IL20 cytokines (e.g. blocking anti-IL-20Rβ antibodies) to limit the susceptibility to infection in COPD mice potentially through an increased production of IL-22.

REFERENCES

Throughout this application, various references describe the state of the art to which this invention pertains. The disclosures of these references are hereby incorporated by reference into the present disclosure.

Pichavant M., Remy, G., Bakaert, S., Le Rouzic, O., Kervoaze, G., Vilain, E., Tillie-Leblond., Trottein, F., Gosset, P. 2014. Oxydative-stressed mediated iNKT cell activation is involved in COPD pathogenesis. Mucosal Immunol, 7(3):568-78.

Patent #EP13305916.2 (28/06 2013)."Methods and pharmaceutical compositions for the treatment of acute exacerbations of chronic obstructive pulmonary disease"

David Torres, Audrey Dieudonné, Bernhard Ryffel, Mustapha Si-Tahar, Eva Vilain, Muriel Pichavant, Philippe Lassalle, Francois Trottein, and Philippe Gosset. Double stranded RNA exacerbates pulmonary allergic reaction through Toll-like Receptor 3: implication of airway epithelium and dendritic cells. J Immunol: 2010 ;185(1):451-9.

Pichavant, M., S. Taront, P. Jeannin, L. Breuilh, A. S. Charbonnier, C. Spriet, C. Fourneau, N. Corvaia, L. Heliot, A. Brichet, A. B. Tonnel, Y. Delneste, and P. Gosset. 2006. Impact of Bronchial Epithelium on Dendritic Cell Migration and Function: Modulation by the Bacterial Motif KpOmpA. *J Immunol* 177:5912-5919.

Engelmann I., Mordacq C., Tillie-Leblond I., Gosset P., Dewilde A., Pouessel G, Deschildre A. Rhinovirus and asthma: re-infection, not persistence. 2013. Am J Respir Crit Care Med, 2013 Nov. 1;188(9):1165-7.

Mear J B, Gosset P, Kipnis E, Faure E, Dessein R, Jawhara S, Fradin C, Faure K, Poulain D, Sendid B, Guery B. Candida albicans airway exposure primes the lung innate immune response against *Pseudomonas aeruginosa* infection through innate lymphoid cell recruitment and IL-22 associated mucosal response. Infect Immun. 2014 January;82(1):306-15.

Faure E, Mear J B, Faure K, Normand S, Couturier-Maillard A, Grandjean T, Balloy V, Ryffel B, Dessein R, Chignard M, Uyttenhove C, Guery B, Gosset P, Chamaillard M, Kipnis E. *Pseudomonas aeruginosa* Type-3 secretion system dampens host defense by exploiting the NLRC4-coupled inflammasome. Am J Respir Crit Care Med, 2014; 189:799-811.

The invention claimed is:

1. A method of treating acute exacerbation of chronic obstructive pulmonary disease (COPD) in a subject having a defective response to a respiratory infection caused by bacteria, comprising administering to the subject a therapeutically effective amount of an antibody against IL-20 receptor subunit beta; wherein the defective response to the infection caused by bacteria is decreased production of IL-17 and IL-22 by blood mononuclear cells (MNC), compared to healthy control subjects, upon exposure to the bacteria; and wherein the production of IL-17 and IL-22 by the MNC is measured in an ELISA assay after the MNC from the subject are stimulated with *S. pneumoniae* or PHA in vitro.

2. The method of claim 1, wherein the bacteria are *Streptococcus pneumoniae, Haemophilus influenzae*, and/or *Moraxella catarrhalis*.

3. The method of claim 1, wherein the antibody against IL-20 receptor subunit beta is the monoclonal antibody 20RNTC.

4. The method of claim 1, wherein the subject is a frequent exacerbator.

5. The method of claim 4, wherein the subject is undergoing treatment for COPD and experiences at least 2 acute exacerbations during a 12-month period.

6. The method of claim 5, wherein the subject experiences 3 or more acute exacerbations during a 12-month period.

* * * * *